United States Patent
Volkmann et al.

(10) Patent No.: US 11,738,198 B2
(45) Date of Patent: Aug. 29, 2023

(54) SYSTEM TO OPTIMIZE ANODIC STIMULATION MODES

(71) Applicant: THE FREESTATE OF BAVARIA REPRESENTED BY THE JULIUS-MAXIMILIANS-UNIVERSITÄT WÜRZBRG, Würzburg (DE)

(72) Inventors: Jens Volkmann, Würzburg (DE); Frank Steigerwald, Würzburg (DE)

(73) Assignee: THE FREESTATE OF BAVARIA REPRESENTED BY THE JULIUS MAXIMILIANS-UNIVERSITÄT WÜRZBRG, Würzburg (DE)

( * ) Notice: Subject to any disclaimer, the term of this patent is extended or adjusted under 35 U.S.C. 154(b) by 757 days.

(21) Appl. No.: 16/869,891

(22) Filed: May 8, 2020

(65) Prior Publication Data

US 2020/0353260 A1  Nov. 12, 2020

Related U.S. Application Data

(60) Provisional application No. 62/846,325, filed on May 10, 2019.

(51) Int. Cl.
*A61N 1/36* (2006.01)

(52) U.S. Cl.
CPC ..... *A61N 1/36139* (2013.01); *A61N 1/36067* (2013.01); *A61N 1/36178* (2013.01)

(58) Field of Classification Search
None
See application file for complete search history.

(56) References Cited

U.S. PATENT DOCUMENTS

| | | | |
|---|---|---|---|
| 4,520,825 | A | 6/1985 | Thompson et al. |
| 4,964,407 | A | 10/1990 | Baker, Jr. et al. |
| 6,181,969 | B1 | 1/2001 | Gord |
| 6,246,912 | B1 | 6/2001 | Sluijter et al. |
| 6,516,227 | B1 | 2/2003 | Meadows et al. |
| 6,560,490 | B2 | 5/2003 | Grill et al. |
| 7,024,247 | B2 | 4/2006 | Gliner et al. |
| 7,424,322 | B2 | 9/2008 | Lombardi et al. |
| 7,450,992 | B1 | 11/2008 | Cameron |

(Continued)

FOREIGN PATENT DOCUMENTS

| | | |
|---|---|---|
| EP | 3381507 | 10/2018 |
| WO | 2014/005075 | 1/2014 |
| WO | 2014/130865 | 8/2014 |

OTHER PUBLICATIONS

Grill, WM and Mortimer, JT. "Stimulus waveforms for selective neural stimulation." IEEE EMBS. vol. 14(4) 1995.

(Continued)

*Primary Examiner* — Jon Eric C Morales
(74) *Attorney, Agent, or Firm* — Lewis & Reese, PLLC

(57) ABSTRACT

Methods of providing neuromodulation therapy to a patient are disclosed herein. In particular, methods of applying deep brain stimulation (DBS) for the treatment of Parkinson's disease (PD) and related disorders are disclosed. Aspects of the methods involve using stimulation waveforms having a first polarity (e.g., cathodic stimulation) to determine an optimum arrangement of electrodes for providing the therapy (i.e., identifying a sweet-spot for stimulation). Therapy is then provided using the optimum arrangement of electrodes to deliver stimulation waveforms having the opposite polarity (e.g., anodic stimulation).

20 Claims, 7 Drawing Sheets

(56) References Cited

U.S. PATENT DOCUMENTS

| | | |
|---|---|---|
| 7,734,340 B2 | 6/2010 | De Ridder |
| 7,890,182 B2 | 2/2011 | Parramon et al. |
| 8,224,453 B2 | 7/2012 | De Ridder |
| 8,255,057 B2 | 8/2012 | Fang et al. |
| 8,335,664 B2 | 12/2012 | Eberle |
| 8,364,273 B2 | 1/2013 | De Ridder |
| 8,401,655 B2 | 3/2013 | De Ridder |
| 8,412,345 B2 | 4/2013 | Moffitt |
| 8,463,402 B2 | 6/2013 | Zhu et al. |
| 8,606,362 B2 | 12/2013 | He et al. |
| 8,620,436 B2 | 12/2013 | Parramon et al. |
| 8,644,947 B2 | 2/2014 | Zhu et al. |
| 8,712,534 B2 | 4/2014 | Wei |
| 8,731,679 B2 | 5/2014 | Ternes et al. |
| 8,761,897 B2 | 6/2014 | Kaula et al. |
| 8,768,453 B2 | 7/2014 | Parramon et al. |
| 8,774,927 B2 | 7/2014 | De Ridder |
| 8,897,870 B2 | 11/2014 | De Ridder |
| 8,934,981 B2 | 1/2015 | De Ridder |
| 9,044,155 B2 | 6/2015 | Strahl |
| 9,061,140 B2 | 6/2015 | Shi et al. |
| 9,089,704 B2 | 7/2015 | Kelly |
| 9,119,964 B2 | 9/2015 | Marnfeldt |
| 9,248,274 B2 | 2/2016 | Troosters et al. |
| 9,259,574 B2 | 2/2016 | Aghassian et al. |
| 9,302,112 B2 | 4/2016 | Bornzin et al. |
| 9,358,391 B2 | 6/2016 | Zhu et al. |
| 9,403,013 B2 | 8/2016 | Walker et al. |
| 9,409,020 B2 | 8/2016 | Parker |
| 9,446,243 B2 | 9/2016 | Marnfeldt et al. |
| 9,462,398 B2 | 10/2016 | De Ridder |
| 9,511,227 B2 | 12/2016 | Biele et al. |
| 9,511,232 B2 | 12/2016 | Biele et al. |
| 9,526,897 B2 | 12/2016 | Chen et al. |
| 9,526,899 B2 | 12/2016 | Biele et al. |
| 9,550,062 B2 | 1/2017 | Khalil et al. |
| 9,656,077 B2 | 5/2017 | De Ridder |
| 9,724,508 B2 | 8/2017 | Lamont et al. |
| 9,731,116 B2 | 8/2017 | Chen |
| 9,737,718 B2 | 8/2017 | Biele et al. |
| 9,849,285 B2 | 12/2017 | Lee et al. |
| 10,076,667 B2 | 9/2018 | Kaula et al. |
| 2006/0015153 A1 | 1/2006 | Gliner et al. |
| 2006/0173493 A1 | 8/2006 | Armstrong et al. |
| 2008/0294211 A1 | 11/2008 | Moffitt |
| 2008/0319497 A1 | 12/2008 | Griffith et al. |
| 2009/0157155 A1 | 6/2009 | Bradley |
| 2011/0009923 A1 | 1/2011 | Lee |
| 2011/0106215 A1 | 5/2011 | Moffitt |
| 2011/0112609 A1 | 5/2011 | Peterson |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2012/0172946 A1 | 7/2012 | Alataris et al. |
| 2012/0191153 A1 | 7/2012 | Swerdlow et al. |
| 2013/0116751 A1 | 5/2013 | Moffitt et al. |
| 2013/0184794 A1 | 7/2013 | Feldman et al. |
| 2013/0289665 A1 | 10/2013 | Marnfeldt et al. |
| 2014/0277267 A1 | 9/2014 | Vansickle et al. |
| 2015/0080982 A1 | 3/2015 | Funderburk |
| 2015/0157861 A1 | 6/2015 | Aghassian |
| 2015/0231402 A1 | 8/2015 | Aghassian |
| 2015/0360038 A1 | 12/2015 | Zottola et al. |
| 2016/0184591 A1 | 6/2016 | Feldman et al. |
| 2016/0220820 A1 | 8/2016 | Zottola |
| 2017/0259065 A1 | 9/2017 | Baru et al. |
| 2017/0281958 A1 | 10/2017 | Serrano Carmona et al. |
| 2017/0348530 A1 | 12/2017 | Doan et al. |
| 2018/0064930 A1 | 3/2018 | Zhang et al. |
| 2018/0071513 A1 | 3/2018 | Weiss et al. |
| 2018/0071515 A1 | 3/2018 | Weiss et al. |
| 2018/0071520 A1 | 3/2018 | Weerakoon et al. |
| 2018/0071527 A1 | 3/2018 | Feldman et al. |
| 2018/0140831 A1 | 5/2018 | Feldman et al. |
| 2018/0272124 A1 | 5/2018 | Feldman et al. |
| 2018/0264278 A1 | 9/2018 | Laghi |
| 2019/0076659 A1 | 3/2019 | Steinke et al. |
| 2019/0083796 A1 | 3/2019 | Weerakoon et al. |
| 2019/0099606 A1 | 4/2019 | Shah et al. |
| 2019/0134383 A1 | 5/2019 | Brill et al. |
| 2019/0175915 A1 | 6/2019 | Brill et al. |
| 2019/0184180 A1 | 6/2019 | Zhang et al. |
| 2019/0329024 A1 | 10/2019 | Kothandaraman et al. |
| 2019/0329025 A1 | 10/2019 | Moffitt et al. |
| 2019/0329039 A1 | 10/2019 | Marnfeldt et al. |
| 2020/0001091 A1 | 1/2020 | Marnfeldt |

OTHER PUBLICATIONS

Kirsch AD, et al., "Anodic Versus Cathodic Neurostimulation of the Subthalamic Nucleus: A Randomized-Controlled Study of Acute Clinical Effects," Parkinsonism and Related Disorders, 55, 2018, pp. 61-67.

McIntyre CC, Grill WM., "Selective Microstimulation of Central Nervous System Neurons," Ann Biomed Eng., Mar. 2000, 28(3):219-33.

McIntyre CC, Grill WM., "Excitation of Central Nervous System Neurons by Nonuniform Electric Fields," Biophys Journal, vol. 76(2), Feb. 1999, pp. 878-888.

Merrill, Daniel R., et al., "Electrical Stimulation of Excitable Tissue: Design of Efficacious and Safe Protocols," Journal of Neuroscience Methods, 141, 2005, pp. 171-198.

Part No. MSP430 data sheet, manufactured by Texas Instruments, retrieved from <http://www.ti.com/lsds/ti/microcontroller/16-bit_msp430/overview.page?DCMP=MCU_other&HQS=msp430>.

Vercise PC Deep Brain Stimulation System: Vercise Navigator 1.0 Programming Guide, Boston Scientific, NM-320907-AA, Jan. 2016, 16 pages.

Wolter, Tilman, "Spinal Cord Stimulation for Neuropathic Pain: Current Perspectives," Journal of Pain Research, Nov. 18, 2014, 7, pp. 651-663.

Hennings, Kristian, et al., "Orderly Activation of Human Motor Neurons Using Electrical Ramp Prepulses," Clinical Neurophysiology, 116, 2005, pp. 597-604.

H.M. Loke, "Tutorial: 2-D and 3-D Electrical Imaging Surveys," (2004), published at https://sites.ualberta.ca/ ~unsworth/ UA-classes/ 223/ loke_course_notes.pdf.

W. Daily et al., "Electrical Resistance Tomography—Theory and Practice," Near-Surface Geophysics Part 2: Applications and Case Histories, Chap. 17, pp. 573-598 (2005).

"Electrical Impedance Tomography," published at https:// en.wikipedia.org/ wiki/Electrical_impedance_tomography.

"Electrical Capacitance Volume Tomography," published at https:// en.wikipedia.org/ wiki/Electrical_capacitance_volume_tomography.

Guide™ DBS Software Programming Manual: Directions for Use, Boston Scientific, 91062299-02 REV A, published at http://www.bostonscientific.com/content/dam/Manuals/eu/current-rev-en/91062299-02_RevA_GUIDE_DBS_Software_Programming_Manual_DFU_multi_OUS_s.pdf (date unknown).

BeMent, Spencer L., et al., "A Quantitative Study of Electrical Stimulation of Central Myelinated Fibers," Experimental Neurology, 24, pp. 147-170, 1969.

Frank, K., et al., "Stimulation of Spinal Motoneurones with Intracellular Electrodes," J. Physiol., 134, pp. 451-470, 1956.

Basser, Peter J., et al., "New Currents in Electrical Stimulation of Excitable Tissues," Annu. Rev. Biomed. Eng., 02, pp. 377-397, 2000.

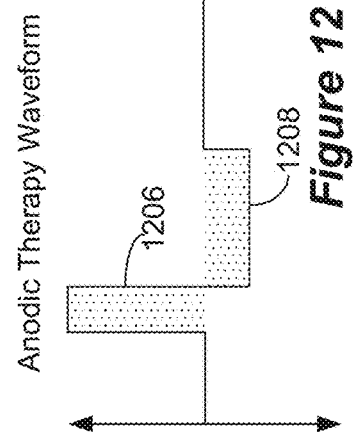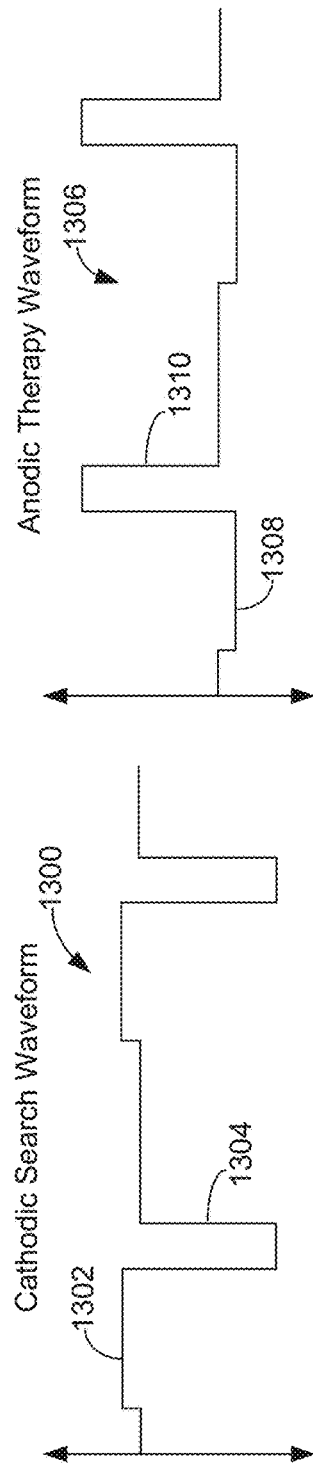
Figure 11
Figure 12
Figure 13

SYSTEM TO OPTIMIZE ANODIC STIMULATION MODES

CROSS REFERENCE TO RELATED APPLICATIONS

This is a non-provisional of U.S. Provisional Patent Application Ser. No. 62/846,325, filed May 10, 2019, which is incorporated herein by reference in its entirety, and to which priority is claimed.

FIELD OF THE TECHNOLOGY

The present disclosure relates to techniques for providing neuromodulation therapy to a patient, and more particularly, for determining an optimum arrangement of electrodes for providing therapy and for providing optimum therapy.

INTRODUCTION

Implantable stimulation devices are devices that generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will focus primarily on the use of the disclosed techniques within a Deep Brain Stimulation (DBS) system, such as is disclosed in U.S. Patent Application Publication No. 2013/0184794. However, the disclosed techniques may find applicability in the context of any implantable medical device or implantable medical device system.

DBS of the subthalamic nucleus (STN) is a well-established therapy for advanced Parkinson's disease (PD). While effectiveness and relative safety of DBS in PD have been proven in various clinical trials, there is little clinical evidence for the majority of commonly used stimulation parameters. Their choice is typically based on clinical experience, expert consensus or trained habits and dictated by technical restrictions of commercial DBS systems. With the advent of next generation neurostimulation devices a wider parameter space has been opened for clinical use.

Effects of DBS depend on the amplitude, frequency and waveform characteristics of the stimulation pulses, geometry and spatial distribution of the applied electrical field and properties of the stimulated tissue, such as distribution and orientation of cell bodies and axons, the topography of network connections and possibly also the underlying pathophysiology of different disease states. It is well accepted that no single mechanism accounts for the effects of DBS in various brain regions and in different diseases. There is thus a need in the art for methods of optimizing therapeutic parameters for treating a patients' symptoms.

SUMMARY

Disclosed herein is a method of determining electrical stimulation parameters for a patient therapy that uses a leadwire implantable in a patient and comprises one or more electrodes. According to some embodiments, the method comprises: applying a search waveform at a plurality of arrangements of the one or more electrodes to determine an arrangement of electrodes and stimulation parameters that provides a therapeutic effect for the patient, and applying a therapy waveform based on the determined arrangement of electrodes and stimulation parameters, wherein the search waveform comprises at least a first leading phase having a first polarity, wherein the first leading phase is a first phase that has an amplitude absolute value equal to or greater than an amplitude absolute value of any other phase of the search waveform, and wherein the therapy waveform comprises at least a second leading phase having a second polarity opposite to the first polarity, wherein the second leading phase is a first phase that has an amplitude absolute value equal to or greater than an amplitude absolute value of any other phase of the therapy waveform. According to some embodiments, the leadwire is implanted in the patient's brain. According to some embodiments, the search waveform comprises a monophasic waveform comprising one or more cathodic phases, and wherein the therapy waveform comprises a monophasic waveform comprising one or more anodic phases. According to some embodiments, the search waveform comprises a multiphasic waveform comprising a leading cathodic phase followed by an anodic active charge recovery phase. According to some embodiments, the search waveform comprises an anodic phase preceding a leading cathodic phase, wherein the anodic phase has a lower amplitude absolute value than the leading cathodic phase. According to some embodiments, the therapy waveform comprises a multiphasic waveform comprising a leading anodic phase followed by a cathodic active charge recovery phase. According to some embodiments, an amplitude absolute value of the leading anodic phase is the same as an amplitude absolute value of the cathodic active charge recovery phase. According to some embodiments, an amplitude absolute value of the leading anodic phase is greater than an amplitude absolute value of the cathodic active charge recovery phase. According to some embodiments, the therapy waveform comprises a cathodic phase preceding a leading anodic phase, wherein the cathodic phase has a lower amplitude absolute value than the leading anodic phase. According to some embodiments, an amplitude absolute value of the leading phase of the therapy waveform is greater than an amplitude absolute value of the leading phase of the search waveform. According to some embodiments, the method further comprises determining a therapeutic window for stimulation using the first polarity, determining a therapeutic window for stimulation using the second polarity, and treating the patient with stimulation using whichever of the first polarity and the second polarity has the largest therapeutic window. According to some embodiments, the method further comprises: determining an adverse effect threshold for stimulation using the first polarity, determining an adverse effect threshold for stimulation using the second polarity, and treating the patient with stimulation using whichever of the first polarity and the second polarity has the greatest adverse effect threshold. According to some embodiments, the method further comprises: determining an indication of clinical effectiveness of stimulation using the first polarity, determining an indication of clinical effectiveness of stimulation using the second polarity, and treating the patient with stimulation using whichever of the first polarity and the second polarity has the greatest clinical effectiveness. According to some embodiments, the indications of clinical effectiveness comprise Unified Parkinson Disease Rating Scale (UPDRS) ratings. According to some embodiments, the method further comprises: determining an indication of the patient's satisfaction with stimulation using the first polarity, determining an indication of the patient's satisfaction with stimulation using the second polarity, and treating the patient with stimulation using whichever of the first polarity and the second polarity has the greatest patient's satisfaction. According to some embodiments, the effective arrangement of electrodes comprises a single electrode at which the search waveform is applied. According to some embodiments, the effective arrangement of electrodes comprises a plurality of electrodes among which the search waveform is fractionated. According to some embodiments, the method further comprises adjusting an amplitude value of the therapy waveform. According to some embodiments, the adjusting comprises lowering.

Also disclosed herein is a non-transitory computer readable medium executable on an external controller configured to communicate with an implantable medical device (IMD) comprising an implantable pulse generator (IPG) and a leadwire implantable in a patient and comprising one or more electrodes, wherein the non-transitory computer readable medium comprises instructions, which when executed by the external controller, configure the external controller to: apply a search waveform at a plurality of arrangements of the one or more electrodes to determine an arrangement of electrodes and stimulation parameters that provides a therapeutic effect for the patient, and apply a therapy waveform based on the determined arrangement of electrodes and stimulation parameters, wherein the search waveform comprises at least a first leading phase having a first polarity, wherein the first leading phase is a first phase that has an amplitude absolute value equal to or greater than an amplitude absolute value of any other phase of the search waveform, and wherein the therapy waveform comprises at least a second leading phase having a second polarity opposite to the first polarity, wherein the second leading phase is a first phase that has an amplitude absolute value equal to or greater than an amplitude absolute value of any other phase of the therapy waveform. According to some embodiments, the search waveform comprises a monophasic waveform comprising one or more cathodic phases, and the therapy waveform comprises a monophasic waveform comprising one or more anodic phases. According to some embodiments, the search waveform comprises a multiphasic waveform comprising a leading cathodic phase followed by an anodic active charge recovery phase and the therapy waveform comprises a multiphasic waveform comprising a leading anodic phase followed by a cathodic active charge recovery phase. According to some embodiments, the search waveform comprises an anodic phase preceding a leading cathodic phase, wherein the anodic phase has a lower amplitude absolute value than the leading cathodic phase and the therapy waveform comprises a cathodic phase preceding a leading anodic phase, wherein the cathodic phase has a lower amplitude absolute value than the leading anodic phase. According to some embodiments, an amplitude absolute value of the leading phase of the therapy waveform is greater than an amplitude absolute value of the leading phase of the search waveform. According to some embodiments, the instructions further configure the external controller to: determine a therapeutic window for stimulation using the first polarity, determine a therapeutic window for stimulation using the second polarity, determine an adverse effect threshold for stimulation using the first polarity, and determine an adverse effect threshold for stimulation using the second polarity. According to some embodiments, the instructions further configure the external controller to: determine an indication of clinical effectiveness of stimulation using the first polarity, determine an indication of clinical effectiveness of stimulation using the second polarity, and enable the IMD to treat the patient with stimulation using whichever of the first polarity and the second polarity has the greatest clinical effectiveness. According to some embodiments, the instructions further configure the external controller to: determine an indication of the patient's satisfaction with stimulation using the first polarity, determine an indication of the patient's satisfaction with stimulation using the second polarity, and enable the IMD to treat the patient with stimulation using whichever of the first polarity and the second polarity has the greatest patient's satisfaction. According to some embodiments, the effective arrangement of electrodes comprises a single electrode at which the search waveform is applied. According to some embodiments, the effective arrangement of electrodes comprises a plurality of electrodes among which the search waveform is fractionated. According to some embodiments, the instructions further configure the external controller to adjust an amplitude value of the therapy waveform. According to some embodiments, the adjusting comprises lowering.

BRIEF DESCRIPTION OF THE DRAWINGS

FIG. 11 illustrates a biphasic cathodic search waveform and a biphasic anodic therapy waveform.

FIG. 12 illustrates an alternative embodiment of a biphasic anodic therapy waveform.

FIG. 13 illustrates search and therapy waveforms having pre-pulse phases preceding the leading phases.

DETAILED DESCRIPTION

Figure 1:
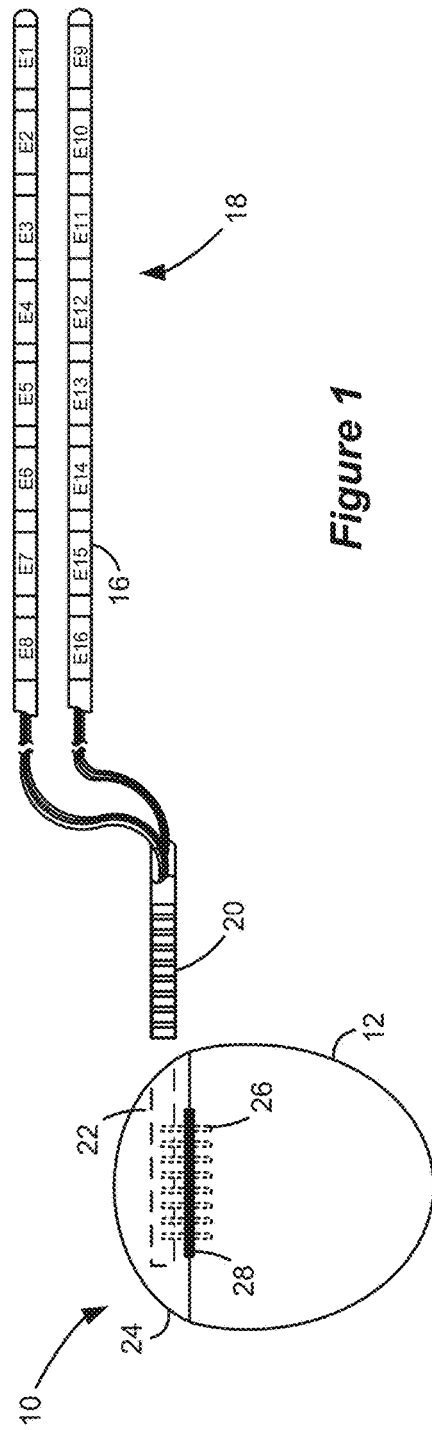
FIG. 1 shows an implantable pulse generator (IPG) with an electrode array.

As shown in FIG. 1, a DBS system typically includes an implantable pulse generator (IPG) 10 (or an implantable medical device, more generally), which includes a biocompatible device case 12 that is formed from a metallic material such as titanium. The case 12 typically comprises two components that are welded together, and it holds the circuitry and battery 14 (FIG. 2) necessary for the IPG 10 to function. The battery 14 may be either rechargeable or primary (non-rechargeable) in nature. The IPG 10 is coupled to electrodes 16 via one or more electrode leads 18 (two of which are shown). The proximal ends of the leads 18 include electrode terminals 20 that are coupled to the IPG 10 at one or more connector blocks 22 fixed in a header 24, which can comprise an epoxy for example. Contacts in the connector blocks 22 make electrical contact with the electrode terminals 20 and communicate with the circuitry inside the case 12 via feedthrough pins 26 passing through a hermetic feedthrough 28 to allow such circuitry to provide stimulation to or monitor the various electrodes 16. The feedthrough assembly 28, which is typically a glass, ceramic, or metallic material, is affixed to the case 12 at its edges to form a hermetic seal. In the illustrated system, there are sixteen electrodes 16 split between two leads 18, although the number of leads and electrodes is application specific and therefore can vary.

Figure 2:
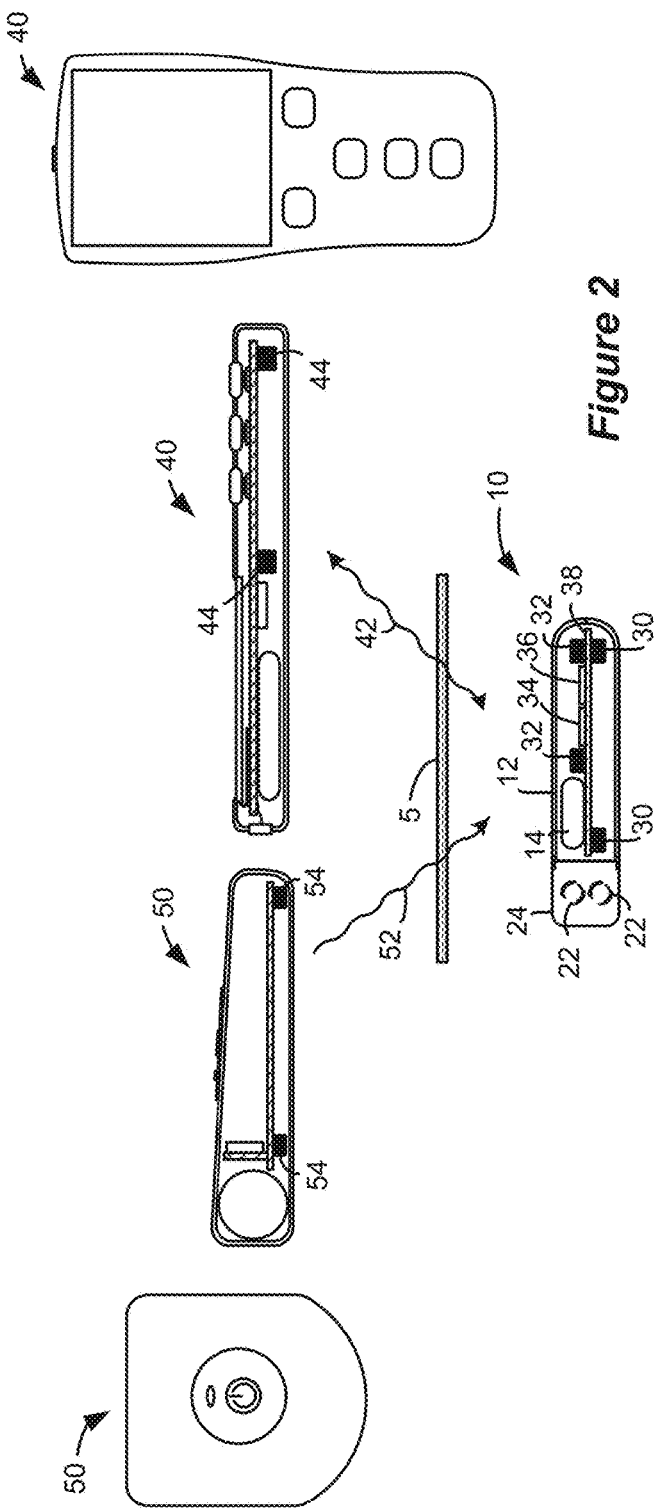
FIG. 2 shows a cross section of the IPG of FIG. 1 as implanted in a patient, as well as external devices that support the IPG, including an external charger and external controller.

As shown in FIG. 2, IPG 10 contains a charging coil 30 for wireless charging of the IPG's battery 14 using an external charging device 50, assuming that battery 14 is a rechargeable battery. If IPG 10 has a primary battery 14, charging coil 30 in the IPG 10 and external charger 50 can be eliminated. IPG 10 also contains a telemetry coil antenna 32 for wirelessly communicating data with an external controller device 40, which is explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include current generation circuitry for providing stimulation pulses at one or more of the electrodes 16 and may also include telemetry modulation and demodulation circuitry for enabling bidirectional wireless communications at antenna 32, battery charging and protection circuitry couplable to charging coil 30, DC-blocking capacitors in each of the current paths proceeding to the electrodes 16, etc. Components within the case 12 are integrated via a printed circuit board (PCB) 38.

FIG. 2 further shows the external components referenced above, which may be used to communicate with the IPG 10, in plan and cross section views. External controller 40 may be used to control and monitor the IPG 10 via a bidirectional wireless communication link 42 passing through a patient's tissue 5. For example, the external controller 40 may be used to provide or adjust a stimulation program for the IPG 10 to execute that provides stimulation to the patient. The stimulation program may specify a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated via Frequency Shift Keying (FSK) or the like, to encode transmitted data. For example, data telemetry via FSK can occur around a center frequency of fc=125 kHz, with a 129 kHz signal representing transmission of a logic '1' bit and 121 kHz representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a hand-holdable, portable housing.

External charger 50 provides power to recharge the IPG 10's battery 14 should that battery be rechargeable. Such power transfer occurs by energizing a charging coil 54 in the external charger 50, which produces a magnetic field comprising transcutaneous link 52, which may occur with a different frequency (f2=80 kHz) than data communications on link 42. This magnetic field 52 energizes the charging coil 30 in the IPG 10, which is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

Figure 3:
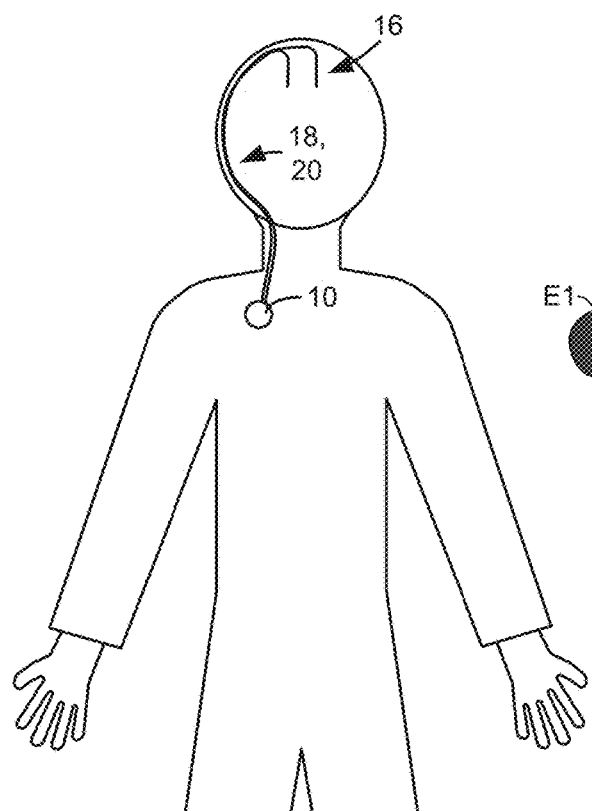
FIG. 3 shows implantation of the IPG in a patient in a Deep Brain Stimulation (DBS) application.

In a DBS application, as is useful in the treatment of neurological disorders such as Parkinson's disease (PD), the IPG 10 is typically implanted under the patient's clavicle (collarbone), and the leads 18 are tunneled through the neck and between the skull and the scalp where the electrodes 16 are implanted through holes drilled in the skull in the left and right sides of the patient's brain, as shown in FIG. 3. Specifically, the electrodes 16 may be implanted in the subthalamic nucleus (STN), the pedunculopontine nucleus (PPN), or the globus pallidus internus (GPi). Stimulation therapy provided by the IPG 10 has shown promise in reducing the symptoms of neurological disorders, including rigidity, bradykinesia, tremor, gait and turning impairment, postural instability, freezing, arm swing, balance impairment, and dystonia.

Figure 4:
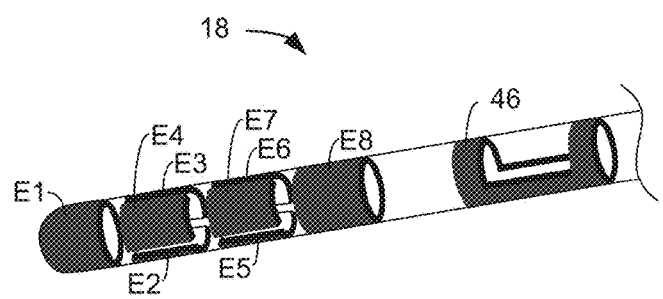
FIG. 4 shows an electrode lead having segmented electrodes as may be used in a DBS application.

While FIG. 1 generically illustrates the electrodes 16 as aligned linearly along a lead 18, electrode leads 18 for DBS applications commonly include segmented electrodes that allow for directional control of stimulation. The electrode lead 18 in FIG. 4 includes multiple circumferential (or ring) electrodes and multiple segmented electrodes. In particular, electrodes E1 and E8 are circumferential electrodes that extend around the circumference of the lead 18 while electrodes E2-E7 are segmented electrodes. As used herein, segmented electrodes refer to electrodes that do not extend fully around the perimeter of an electrode lead 18. In the illustrated embodiment, the segmented electrodes are arranged with three electrodes at a particular axial position, each segmented electrode spanning an approximately 90 degree arc around the lead 18 with approximately 30 degree spaces between neighboring segmented electrodes. Although a particular example of a lead is illustrated in FIG. 4, the type and placement of electrodes 16 along a lead is application specific and therefore can vary. For example, a lead may include more or fewer segmented electrodes at a given axial position and more or fewer circumferential electrodes in addition to the segmented electrodes. As will be understood, because the segmented electrodes are separated by a non-conductive break, electrical stimulation that is directed to a segmented electrode propagates outward in the direction of the electrode rather than uniformly about the lead 18 as with circumferential electrodes. The lead 18 additionally includes a marker 46 that is aligned with segmented electrodes E2 and E5. The marker 46 provides a visual indication of the lead's orientation prior to implantation as well as a radiological indication of the lead's orientation after implantation.

As mentioned above, the electrical stimulation that the IPG 10 is capable of delivering is highly customizable with respect to selected electrodes, current amplitude and polarity, pulse duration, pulse frequency, etc. Due to uncertainties in the location of electrodes with respect to neural targets, the physiological response of a patient to stimulation patterns, and the nature of the electrical environment within which the electrodes are positioned, the stimulation parameters that might provide effective stimulation therapy for a particular patient are typically determined using a trial and error approach. Thus, after the leads are implanted, an initial programming session is typically performed to customize the parameters of the stimulation provided by the IPG 10 to obtain the greatest benefit for the patient. While not common in DBS applications due to the dangers of having externalized leads or lead extensions, in other applications such as spinal cord stimulation (SCS), it is common for the initial programming session to be performed after lead implantation using an external trial stimulator that mimics the operation of the IPG 10 and that is coupled to the implanted leads 18 but is not itself implanted.

Figure 5:
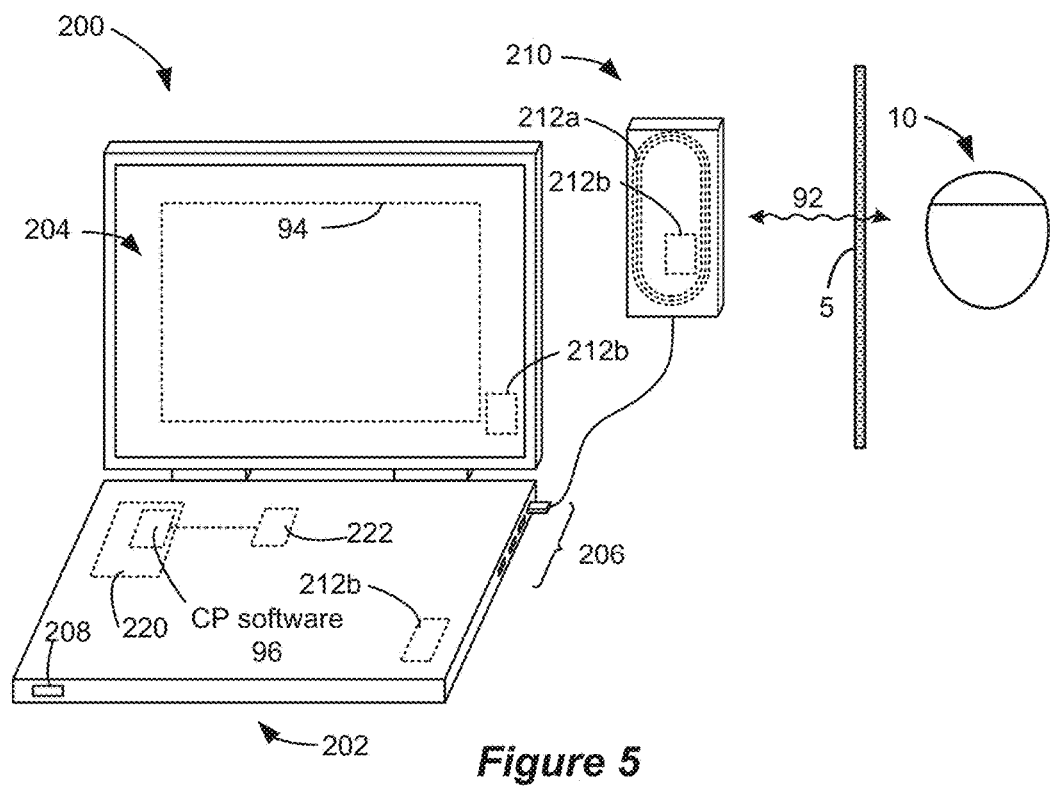
FIG. 5 shows components of a clinician's programmer system, including components for communicating with a neurostimulator such as an IPG.

Referring to FIG. 5, the initial programming is typically performed by communicating different stimulation programs from a clinician's programmer system (CP System) 200 to the IPG 10 and observing the patient's responses to the IPG 10's execution of the different programs. For a DBS application, a clinician may observe the extent to which the current stimulation program decreases the effects of the patient's neurological disorder (e.g., the extent to which the stimulation program decreases the degree of tremor) as well as any side effects induced as a result of the stimulation program. As shown, CP system 200 can comprise a computing device 202, such as a desktop, laptop, or notebook computer, a tablet, a mobile smart phone, a Personal Data Assistant (PDA)-type mobile computing device, etc. (hereinafter "CP computer"). In FIG. 5, CP computer 202 is shown as a laptop computer that includes typical computer user interface means such as a screen 204, a mouse, a keyboard, speakers, a stylus, a printer, etc., not all of which are shown for convenience.

Also shown in FIG. 5 is an accessory communication head 210 that is couplable to a port of the CP computer 202, such as a USB port 206, and that is specific to the CP computer 202's operation as a neurostimulator controller. Communication between the CP system 200 and the IPG 10 may comprise magnetic inductive or short-range RF telemetry schemes (as described above with respect to communications between the IPG 10 and the programmer 40), and in this regard the IPG 10 and the CP computer 202 and/or the communication head 210 (which can be placed proximate to the IPG 10) may include antennas compliant with the telemetry means chosen. For example, the communication head 210 can include a coil antenna 212a, a short-range RF antenna 212b, or both. The CP computer 202 may also communicate directly with the IPG 10, for example using an integral short-range RF antenna 212b, without the use of the communication head 210.

If the CP system 200 includes a short-range RF antenna (either in CP computer 202 or communication head 210), such antenna can also be used to establish communication between the CP system 200 and other devices, and ultimately to larger communication networks such as the Internet. The CP system 200 can typically also communicate with such other networks via a wired link provided at an Ethernet or network port 208 on the CP computer 202, or with other devices or networks using other wired connections (e.g., at USB ports 206).

To test different stimulation parameters during the initial programming session, a user interfaces with a clinician programmer graphical user interface (CP GUI) 94 provided on the display 204 of the CP computer 202. As one skilled in the art understands, the CP GUI 94 can be rendered by execution of CP software 96 on the CP computer 202, which software may be stored in the CP computer 202's non-volatile memory 220. One skilled in the art will additionally recognize that execution of the CP software 96 in the CP computer 202 can be facilitated by control circuitry 222 such as a microprocessor, microcomputer, an FPGA, other digital logic structures, etc., which is capable of executing programs in a computing device. Such control circuitry 222 when executing the CP software 96 will in addition to rendering the CP GUI 94 cause the CP computer 202 to communicate the stimulation parameters to the IPG 10 using a suitable antenna 212a or 212b, either in the communication head 210 or the CP computer 202 as explained earlier. The CP software 96 enables a user to select the type of electrode lead(s) that have been implanted (e.g., from a list of leads that are configured in the software 96) and to customize the stimulation parameters using the available electrodes on the implanted lead. In this way, the user can communicate different stimulation parameters to the IPG 10 for execution to observe the effects of the various parameters and to hone in on the appropriate settings for the patient.

The stimulation parameters that are communicated to the IPG 10 are ultimately converted to control signals that are distributed to one or more Digital-to-Analog Converters (DACs) 72 in the IPG 10's stimulation circuitry to form pulses defined by the stimulation parameters at the selected electrodes. Traditionally, DBS stimulation has involved the periodic application of electrical pulses with one or more lead-based electrodes 16 (i.e., one or more electrodes 16 that are carried on the lead 18 and thus implanted in the region of interest such as the brain) acting as the cathode and the case 12 acting as the anode.

Figure 6:
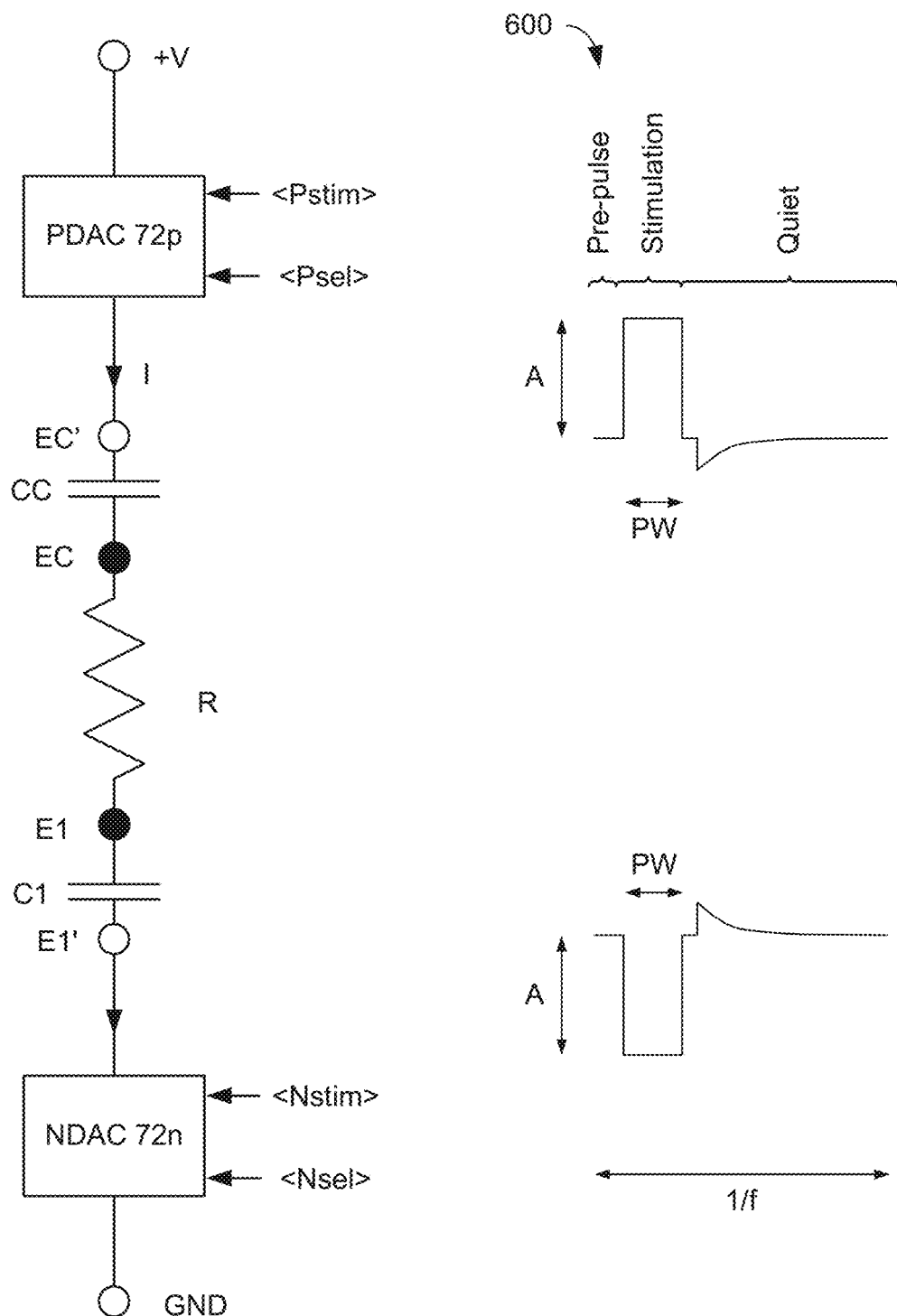
FIG. 6 shows an example of Digital-to-Analog Converter (DAC) circuitry as arranged to generate a square wave pulse.

FIG. 6 shows a simple example of DAC circuitry 72 as arranged to provide a traditional square wave pulse 600 of this type using electrode E1 as the selected lead-based electrode 16. DAC circuitry 72 as shown comprises two portions, denoted as PDAC 72p and NDAC 72n. These portions of DAC circuitry 72 are so named due to the polarity of the transistors used to build them and the polarity of the current they provide. Thus, PDAC 72p is formed from P-channel transistors and is used to source a current +I to the patient's tissue R via a selected electrode operating as an anode, and NDAC 72n is formed of N-channel transistors and is used to sink current −I from the patient's tissue via a selected electrode operating as a cathode. It is important that current sourced to the tissue at any given time equal that sunk from the tissue to prevent charge from building in the tissue, although more than one lead-based electrode 16 may be operable at a given time.

PDAC 72p and NDAC 72n are current sources that receive digital control signals, denoted <Pstim> and <Nstim> respectively, to generate current of a prescribed amplitude at appropriate times. More specifically, PDAC 72p and NDAC 72n include current-mirrored transistors for mirroring (amplifying) a reference current Iref to produce pulses with a specified amplitude. Although the DAC circuitry 72 (PDAC 72p and NDAC 72n) may be dedicated at each of the electrodes and thus may be activated only when its associated electrode is to be selected as an anode or cathode, see, e.g., U.S. Pat. No. 6,181,969, the illustrated example assumes that one or more DACs (or one or more current sources within a DAC) are distributed to a selected electrode by a switch matrix (not shown), and control signals <Psel> and <Nsel> are used to control the switch matrix and establish the connection between the selected electrode and the PDAC 72*p* or NDAC 72*n*.

In the example shown, control signals <Pstim>, <Nstim>, <Psel>, and <Nsel> prescribe the various parameters of the square wave pulse 600. The pulse 600 is defined by multiple phases that include a pre-pulse phase, a stimulation phase, and a quiet phase. During the stimulation phase, current I (having amplitude A) is sourced from the PDAC 72*p* to electrode node EC' (a node in the IPG 10's current generation circuitry that is coupled to the case 12 through a blocking capacitor CC) for a duration PW. From electrode node EC', the current I flows through the blocking capacitor CC to the case 12 (operating as electrode EC). The NDAC 72*n* pulls the current I through the patient's tissue R from electrode E1 through the blocking capacitor C1 and to the electrode node E1' over the same duration PW. In the monophasic type of stimulation that is illustrated, charge that has built up on the blocking capacitors during the stimulation phase is recovered using passive recovery (illustrated as the decaying charge in the quiet phase) during the quiet phase as is known. Alternatively, a recovery phase of opposite polarity may be applied at the selected electrodes following the stimulation phase to recover charge that has built up on the blocking capacitors during the stimulation phase. Although pulses of different types and shapes may be formed, most of the examples in the remainder of this application depict monophasic square wave pulses (with passive recovery indication omitted). It should be noted though, that the application is relevant to pulses of different types and the polarity of a particular pulse is assumed to describe the polarity during an active stimulation phase. In addition, this application is relevant to coordinated reset therapy, which can include anodic coordinated reset therapy, mixed anodic and cathodic coordinated reset therapy, and cathodic coordinated reset therapy.

The PDAC 72*p* and NDAC 72*n* along with the intervening tissue R complete a circuit between a power supply +V and ground. The compliance voltage +V is adjustable to an optimal level to ensure that current pulses of a prescribed amplitude can be produced without unnecessarily wasting IPG power. While a single pulse 600 is illustrated, such a pulse is typically repeated in succession and the duration of the single period of the pulse 600 defines the stimulation frequency f.

Traditional DBS programming has focused on the selection of the one or more lead-based electrodes 16, the pulse width, the pulse amplitude, and the stimulation frequency that provides the most effective therapy for the patient. The polarity of the lead-based electrodes 16 during the stimulation phase, however, has not been a customizable parameter of traditional DBS stimulation as it has been considered that only cathodic stimulation at the particular area of interest (i.e., the tissue within which the leads are implanted) is therapeutically effective. Recently, it has been observed that anodic stimulation (i.e., stimulation in which one or more selected lead-based electrodes 16 operate as the anode) can provide beneficial therapeutic effects. It has further been observed that anodic stimulation operates via a different biological mechanism than traditional cathodic stimulation and that the different types of stimulation provide different therapeutic effects.

From the "electro-physical" view point, the DBS system and the patient's body form a closed electrical circuit, in which the implantable pulse generator (IPG) battery is the circuit's electrical source. In monopolar mode, the current flows through the lead wires to the activated DBS-electrodes, across the electrode-tissue interface and back through the tissue to the IPG case. In principle, a stimulating electrode can act as an anode (+, source of current) or a cathode (−, sink of current) and the case can act as the counter-electrode, i.e., with opposite polarity than the lead electrode. First generation DBS devices restricted the monopolar montage to cathodic brain stimulation by always activating the IPG case as an anode. This choice was supported by experimental data demonstrating that cathodic brain stimulation elicits behavioral responses more readily than anodic stimulation. Myelinated fibers require a 3-8 times higher anodic than cathodic stimulation amplitude to elicit an action potential, since it is easier to achieve a suprathreshold depolarization close to the cathode. In contrast, electrodes close to a neuronal cell body show only minor differences for anodic and cathodic stimulation strength, sometimes with even lower amplitudes needed with anodic stimulation presumably depending on the geometry of electrode and axon. See, e.g., McIntyre, C. C., and Grill, W. M., "Selective Microstimulation of Central Nervous System Neurons," Ann. Biomed. Eng., 2000, 28(3), 219-33.

Figure 7A:
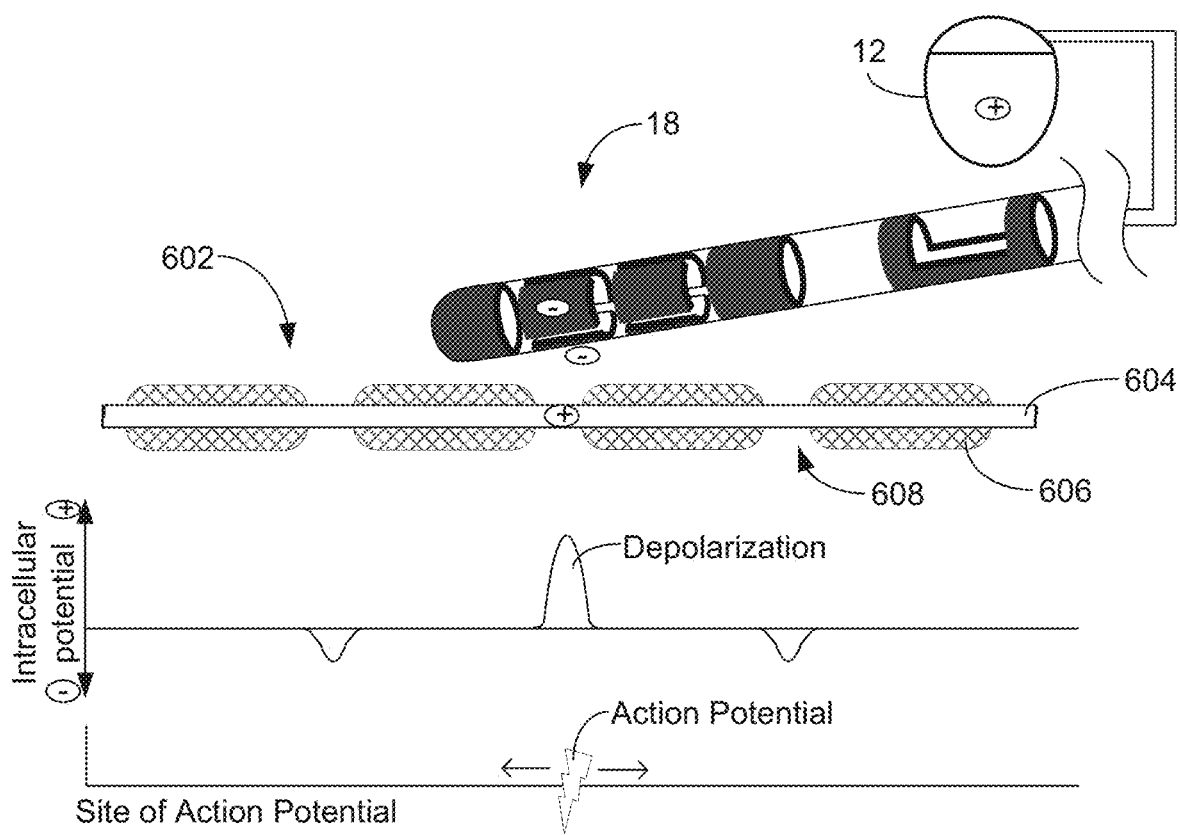
FIGS. 7A and 7B illustrate application of cathodic stimulation (7A) and anodic stimulation (7B) to a neuron.
Figure 7B:
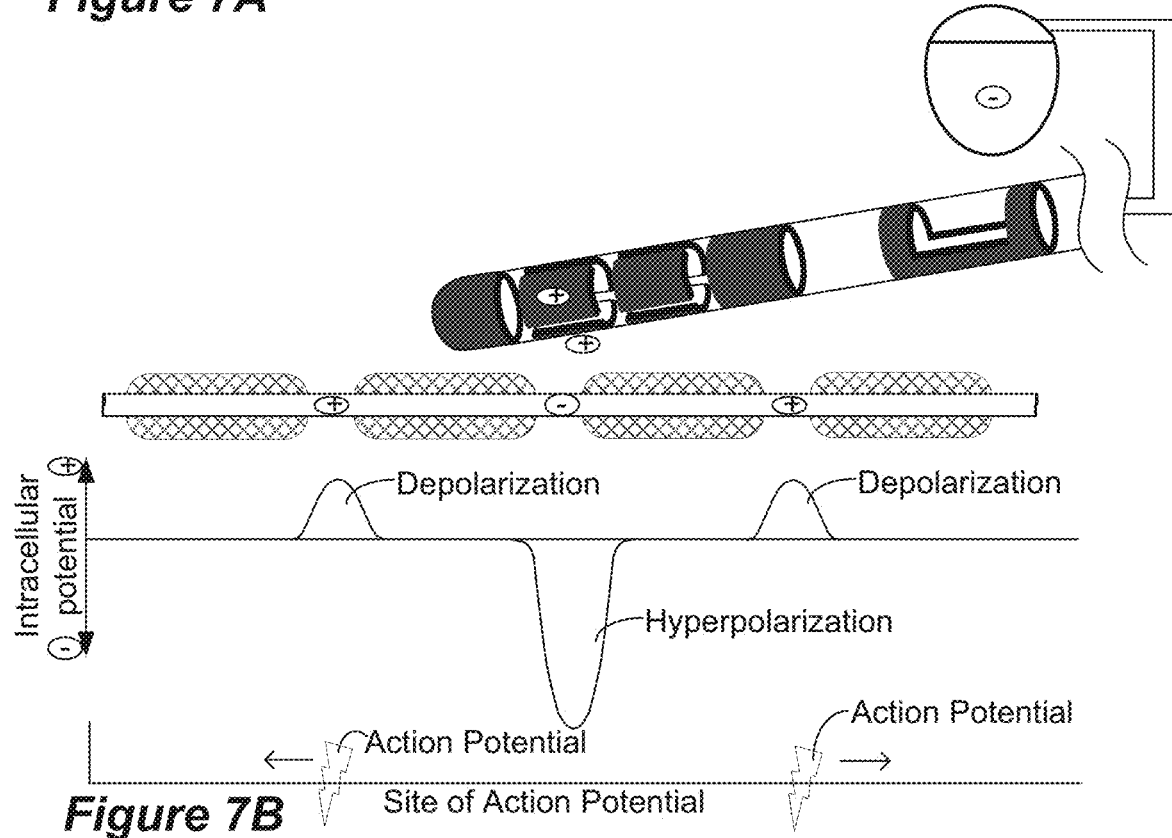

FIG. 7A illustrates a "conventional" cathodic stimulation electrode configuration with the IPG case 12 serving as an anode and two segmented electrodes as cathodes. The electrode lead 18 is placed near a neuron 602. The axon 604, myelin sheath 606, and myelin internodes 608 of the neuron 602 are illustrated. The axon close to the cathode is depolarized, generating an action potential, which propagates ortho- and antidromically. FIG. 7B shows the corresponding stimulation setting with reversed polarity, i.e., configured for anodic stimulation. In FIG. 7B the case 12 serves as a cathode and two segmented electrodes as anodes. The neighboring axon becomes hyperpolarized. Current flow within the axon and across the membrane causes a depolarization at the next myelin internodes, which generate action potentials if a threshold potential is reached.

The inventors have discovered that the use of anodic stimulation for DBS may provide effective therapy for treating a patient's symptoms. In some instances, anodic stimulation may provide a wider therapeutic window (TW) for treating a patient's symptoms. The term therapeutic window (TW) is used herein to refer to the difference between the effect threshold and the adverse effect threshold. The effect threshold is the minimum stimulation intensity that reduces the patient's symptoms. For example, in a patient suffering from PD, the effect threshold may be defined as the stimulation amplitude at which hypotonia or a near complete reduction of rigidity of the contralateral upper limb is induced by the stimulation. The adverse effect threshold may be the stimulation amplitude at which first, non-habituating adverse effects occur, e.g., muscle contraction, dysarthria, prolonged paresthesia, double or blurred vision, etc. The TW can be found by subtracting the effect threshold from the adverse effect threshold.

In one study, the inventors tested a polarity reversal from conventional monopolar cathodic to anodic stimulation in an acute double-blind, randomized, cross-over study of 10 patients with PD implanted with bilateral STN DBS. The study is described in "Anodic versus cathodic neurostimulation of the subthalamic nucleus: A randomized-controlled study of acute clinical effects," Kirsch, et al., Parkinsonism and Related Disorders, 55, (2018), 61-67, the entire contents of which are incorporated herein by reference. Patients with idiopathic PD were implanted with a bilateral STN-DBS system having eight-contact directional leads and an IPG capable of multiple independent current source control (MICC), which allows any electrode as well as the IPG case to be programmed as either cathode (−) or anode (+). Prior to the study, the best clinical responses were achieved with monopolar setting, where the IPG case was the anode and one or more of the electrode contacts were cathodes and only a single program area was active per lead.

Each study patient was screened for the best clinical settings of cathodic stimulation during an extensive monopolar review session to identify the electrode contact combinations with highest efficacy and best TW. Study evaluations started after a minimal 15-minute stimulation washout period, following which the stimulation settings were reversed (i.e., all parameters identical except for reversed polarity). Before evaluating effect and side effect thresholds, patients were evaluated using the full MDS-UPDRS-III baseline in the stimulation OFF condition. The examiner performing the evaluation and the patient remained blinded to the actual stimulation settings for the entire study period. To maintain the blinding, all programming changes were done by an unblinded investigator. The programmer screen was shielded from the view of patient and blinded investigator, who instructed verbally the titration of stimulation amplitude while evaluating clinical responses. Effect threshold was defined as the amplitude at which hypotonia or near complete reduction of rigidity of the contralateral upper limb was induced by stimulation. Adverse effect threshold was the amplitude at which first, non-habituating adverse effects occurred, e.g. muscle contraction, dysarthria, prolonged paresthesia, double or blurred vision. Thresholds were approximated by stepwise increases and decreases of 0.5 mA and then refined in steps of 0.1 mA.

After determining the thresholds for each STN, the amplitude was programmed to 0.5 mA below the adverse effect threshold to ensure a supra-effective stimulation. Motor symptoms were evaluated by scoring MDS-UPDRS-III after a stimulation period of 30 min, followed by at least 15 min stimulation washout and crossover to the second stimulation condition. The sequence of stimulation conditions (anodic vs. cathodic) was balanced.

To assess effects of unilateral stimulation, we calculated a hemibody score of the MDS-UPDRS-III by adding the contralateral rigidity, bradykinesia and tremor items (items no: 3-8 & 15-17). For symptom specific analysis a sum of contralateral rigidity items and a sum of contralateral bradykinesia items of UPDRS-III were calculated. For tremor sub-score the items of contralateral postural, action and rest tremor were added (items no. 15-17).

Effect thresholds were significantly higher in anodic compared to cathodic mode: $3.36 \pm 1.58$ mA vs. $1.99 \pm 1.37$ mA ($p<0.0001$; Wilcoxon-2-sample-test). Likewise, the adverse effect threshold increased significantly from $4.15 \pm 1.13$ mA in cathodic to $6.05 \pm 1.52$ mA in anodic mode ($p<0.0001$ Wilcoxon-2-sample-test). Pyramidal tract stimulation with muscle contractions or fibrillations and dysarthria were the most commonly observed limiting adverse effects. In 70% of electrodes, the type of first limiting adverse effect was identical for cathodic or anodic stimulation. This increase in individual effect threshold ($1.38 \pm 0.99$ mA) was smaller compared to the increase of adverse effect threshold ($1.90 \pm 1.09$ mA) with anodic stimulation, resulting in a wider therapeutic window (TW), calculated by subtracting effect threshold from adverse effect threshold for each individual STN, with anodic stimulation ($2.69 \pm 1.52$ mA vs. $2.17 \pm 1.13$ mA; $p=0.065$ Wilcoxon-2-sample-test). The trend of a larger TW with anodic stimulation became statistically significant ($2.73 \pm 1.43$ mA vs. $2.07 \pm 1.14$ mA, $p<0.05$ Wilcoxon-2-sample-test), if two outliers with very low cathodic effect thresholds were excluded.

Thirty minutes of anodic neurostimulation (with an amplitude set to 0.5 mA below the adverse effect threshold; $5.5 \pm 1.5$ mA) reduced the MDS-UPDRS-III rating of off-period motor signs by 62%, from a median 45 (range 16-61) to 17 points (range 12-25). This was significantly superior to the 49% score reduction associated with cathodic stimulation (median 23, range 12-37 points; $p<0.005$ Mann-Whitney-U-test at $3.7 \pm 1.1$ mA). A similar superiority of anodic stimulation with an amplitude close to the upper margin of the individual TW was observed for the hemibody scores (Med off/Stim off: 14 points (range 5-28); anodic: 4 points (range 0-9); cathodic 7 points (range: 2-18), $p<0.05$ Mann-Whitney-U-test).

To reduce the variance in individual DBS responsiveness and as an independent benchmark for the therapeutic response, an individual stimulation response ratio by comparing the anodic vs. cathodic "stimulation ON" state with the "best medication ON" in the preoperative $_L$-Dopa-challenge challenge using the UPDRS III scores were calculated. Anodic stimulation resulted in a MDS-UPDRS III score improvement, which almost completely matched the $_L$-Dopa effect, while cathodic stimulation reproduced only approximately 70% of the preoperative "best medication ON" ($101 \pm 35.2\%$ vs. $72 \pm 24.5\%$, $p<0.05$ Wil-coxon-2-sample-test). Bradykinesia as well as rigidity sub-scores improved significantly more with anodic than with cathodic stimulation (bradykinesia 58.6% vs. 39.8%, $p<0.05$; rigidity: 92.5% vs. 75.5%, $p<0.02$).

The results described above illustrate that anodic stimulation thresholds are slightly higher than cathodic stimulation thresholds. But unexpectedly, a better clinical effect of anodic compared to cathodic stimulation during an acute stimulation challenge test using supra-effective amplitude settings were observed. This was also confirmed by a secondary analysis benchmarking the stimulation response with the individual levodopa response, in which cathodic stimulation settings achieved only about 70% of the individual levodopa response, while anodic stimulation closely matched the best individual "medication ON".

A behavioral response of brain stimulation results from induced action potential firing in a critical number of neurons altering the activity of a neural circuit. In a clinical setting, these responses can be desirable and alleviate symptoms of abnormal brain function or they may impair intact function, depending on which neural elements are preferentially activated in a small brain volume surrounding the electrode. Anodic stimulation is also known as "virtual cathode" stimulation, because it hyperpolarizes membranes immediately below the electrode, but elicits action potentials at a distance from the electrode via the return current generating a virtual cathodic stimulation at both sides of the anodic hyperpolarization (see FIG. 7B). Depending on the distance and orientation of "good and bad fibers," anodic stimulation may favorably impact the recruitment curve of these pathways. In other words, anodic stimulation may be advantageous in situations when adverse effect fibers (e.g. pyramidal tract) are recruited by cathodic stimulation before a critical number of beneficial fibers is being stimulated to achieve an optimal clinical response. This may depend on the position (site and angle/orientation) of the electrode in relation to the different fiber pathways, which suggests, that optimal anodic and cathodic stimulation volume and thus electrode selection may differ slightly. The different testing amplitudes for anodic and cathodic stimulation by stimulating 0.5 mA below the individual adverse effect threshold in each condition may contribute to the different recruitment of neural elements and hence a better efficacy of anodic stimulation. The expanded amplitude range (i.e., the expanded TW) of anodic stimulation allows clinical improvements close to the "best medication ON", while cathodic stimulation amplitudes are restricted by adverse effects to a range resulting in inferior outcomes.

Figure 8:
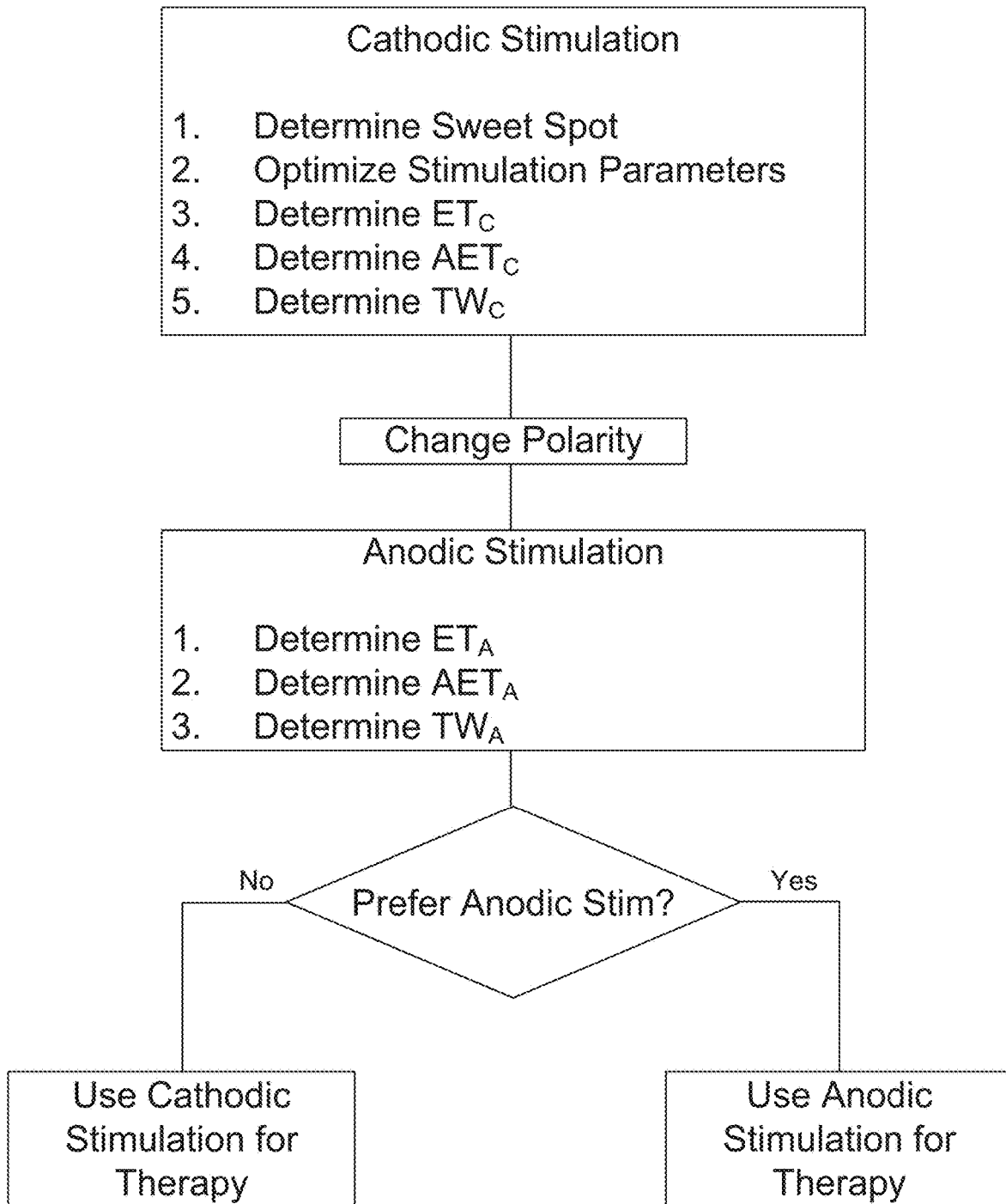
FIG. 8 illustrates a method of identifying optimum stimulation parameters in accordance with an aspect of the disclosure.

Aspects of the disclosure leverage the above-identified beneficial outcomes resulting from anodic stimulation. FIG. 8 outlines a method that uses both cathodic and anodic stimulation. According to some embodiments of the outlined method, cathodic stimulation can be used to determine a desirable or optimal electrode configuration for applying neural modulation to the target neural elements to provide the best therapeutic effect. In other words, cathodic waveforms can be used to determine a "sweet spot" for stimulation.

Figure 9:
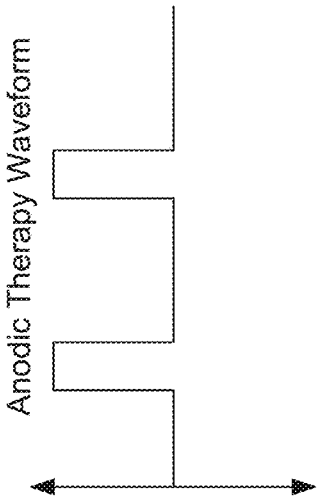
FIG. 9 illustrates an example of sweet-spot searching in accordance with an aspect of the disclosure.

FIG. 9 illustrates an example of using cathodic stimulation to determine an optimal electrode configuration (i.e., sweet-spot searching). In the illustrated embodiment, monopolar stimulation is provided with the current fractionated among different combinations of electrodes. A therapy score is evaluated for each electrode configuration. The therapy score can be determined based on patient feedback, observing the patient response (hypotonia, rigidity, motor symptoms) as described above, or any other evaluation criteria that the physician chooses.

Referring again to FIG. 8, once an optimal electrode configuration (sweet-spot) is identified, the physician may optimize other stimulation parameters, such as the stimulation pulse width, frequency, etc. At that point, the physician may also determine the effect threshold and adverse effect threshold for the cathodic stimulation ($ET_C$ and $AET_C$, respectively). This allows the therapeutic window for the cathodic stimulation $TW_C$ to be determined.

The polarity of the stimulation can be switched, i.e., to anodic stimulation using the determined optimum electrode configuration. Using anodic stimulation, the effect threshold, adverse effect threshold, and therapeutic window ($ET_A$, $AET_A$, and $TW_A$, respectively) can be determined. Based on the comparison of ET, AET, and TW for both cathodic and anodic stimulation, as well as consideration of other factors, a decision can be made to use either anodic or cathodic stimulation for ongoing therapy. For example, the adverse effect threshold for the cathodic stimulation can be compared to the adverse effect threshold for the anodic stimulation. In other words, it can be determined if anodic stimulation provides a greater therapeutic window than cathodic stimulation. If the therapeutic window for anodic stimulation is greater, then the physician may choose to use anodic stimulation for the therapy. In some cases, the physician may choose to use anodic stimulation because anodic stimulation provides a wider TW, even if the effects of the stimulation for anodic and cathodic stimulation are similar. If the anodic stimulation does not provide a greater therapeutic window, then the physician may choose to continue with cathodic stimulation for therapy, for example, if cathodic stimulation may reduce power demands on the IPG. It should be noted that if anodic stimulation is used for therapy, then the physician may further optimize the therapy settings, for example, the pulse width, frequency, etc. According to some embodiments, when anodic stimulation is chosen for the therapy, the amplitude may be set just below the $AET_A$, for example 0.5 mA below $AET_A$, to insure supra-effective therapy.

In some cases, the decision to use anodic stimulation as opposed to cathodic stimulation for ongoing therapy may be based on factors other than (or in addition to) a comparison of the therapeutic windows (TWs.) For example, the patient may simply prefer anodic stimulation. Also, the clinician and patient may see greater clinical improvement based on an indication of clinical effectiveness (e.g., more favorable UPDRS) with anodic stimulation.

Figure 10:
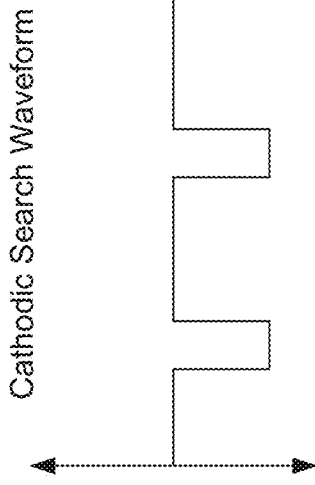
FIG. 10 illustrates a monophasic cathodic search waveform and a monophasic anodic therapy waveform.

Thus, some embodiments of the methods disclosed herein involve using stimulation waveforms having a first polarity (e.g., cathodic) as a search waveform to determine an optimal electrode configuration. Once an optimum electrode configuration is determined, the polarity of the stimulation is switched and a therapy waveform of opposite polarity (e.g., anodic) is applied. FIG. 10 illustrates an example a cathodic search waveform and an anodic therapy waveform. It should be noted that in such an embodiment, a counter electrode (example, the IPG case $E_c$) is used but not illustrated. It should also be noted that the search and therapy waveforms illustrated in FIG. 10 are monophasic. However, the search and therapy waveforms need not be monophasic; they may be multiphasic. For example, FIG. 11 illustrates an embodiment employing biphasic search and therapy waveforms. Note that the cathodic search wave form comprises a cathodic leading phase 1102 and a following anodic active charge recovery phase 1104. Likewise, the anodic therapy waveform comprises an anodic leading phase 1106 and a following cathodic active charge recovery phase 1108. Even though the cathodic waveform includes a following anodic phase, it is still considered a cathodic waveform according to the instant disclosure. Likewise, the anodic therapy waveform is considered an anodic waveform even though it includes a following cathodic phase.

Referring to the waveforms illustrated in FIG. 11, it will be noted that the amplitudes of the leading phase and the active charge recovery phase are the same. However, that need not be case. FIG. 12 illustrates an anodic therapy waveform comprising an anodic leading phase 1206 and a cathodic active charge recovery phase 1208. Note that the cathodic active charge recovery phase 1208 has a smaller amplitude but a longer duration than the anodic leading phase 1206. The area beneath the two phases (showed in filled) is equal such that the two phases pass an equal charge; thus, the charge is essentially completely recovered. According to some embodiments, it may be desirable to use a lower amplitude charge recovery phase, for example, to avoid adverse effects.

FIG. 13 illustrates other examples of a cathodic search waveform and an anodic therapy waveform. The cathodic search waveform 1300 includes a low amplitude "pre-pulse" phase 1302 preceding the main cathodic phase 1304. Within the present disclosure, phase 1304 is considered the "leading phase," even though the low amplitude phase 1302 precedes phase 1304 in time. Note that the waveform 1300 is still considered a "cathodic waveform," as that term is used herein, even though the first phase in time, 1302, is anodic. That is because the first phase of the waveform that has an amplitude equal to or greater than any phase in the waveform (1304) is cathodic. In other words, the "leading phase" of waveform 1300 is cathodic. Likewise, the anodic therapy waveform 1306 includes a low amplitude cathodic "pre-pulse" phase 1308, followed by a higher amplitude anodic phase 1310. Again, waveform 1306 is considered an "anodic" waveform even though the first phase in time is the low amplitude phase 1308, which is cathodic. The term "leading phase" refers to the first phase in a waveform having an amplitude absolute value greater than or equal to any other phase in the waveform.

Various aspects of the disclosed techniques, including processes implementable in the IPG, or in external devices such as the clinician programmer or external controller, for example, to render and operate the GUI, can be formulated and stored as instructions in a computer-readable media associated with such devices, such as in a magnetic, optical, or solid-state memory. The computer-readable media with such stored instructions may also comprise a device readable by the clinician programmer, such as a memory stick or a removable disk, and may reside elsewhere. For example, the computer-readable media may be associated with a server or any other computer device, thus allowing instructions to be downloaded to the clinician programmer system or external controller or to the IPG, via the Internet for example.

Although particular embodiments have been shown and described, it should be understood that the above discussion is not intended to limit the present disclosure to these embodiments. It will be obvious to those skilled in the art that various changes and modifications may be made without departing from the spirit and scope of the present disclosure. Thus, the present disclosure is intended to cover alternatives, modifications, and equivalents that may fall within the spirit and scope of the claims.

What is claimed is:

1. A method of determining electrical stimulation parameters for a patient therapy that uses a leadwire implantable in a patient and comprises one or more electrodes, the method comprising:
    applying a search waveform at a plurality of arrangements of the one or more electrodes to determine an arrangement of electrodes and stimulation parameters that provides a therapeutic effect for the patient, and
    applying a therapy waveform based on the determined arrangement of electrodes and stimulation parameters, wherein
    the search waveform comprises a leading phase having a first polarity and an amplitude absolute value equal to or greater than an amplitude absolute value of any other phase of the search waveform, and wherein
    the therapy waveform comprises a leading phase having a second polarity opposite to the first polarity of the leading phase of the search waveform and having an amplitude absolute value equal to or greater than an amplitude absolute value of any other phase of the therapy waveform.

2. The method of claim 1, wherein the leadwire is implanted in the patient's brain.

3. The method of claim 1, wherein the search waveform comprises a monophasic waveform comprising one or more cathodic phases, and wherein the therapy waveform comprises a monophasic waveform comprising one or more anodic phases.

4. The method of claim 1, wherein the search waveform comprises a multiphasic waveform comprising a leading cathodic phase followed by an anodic active charge recovery phase.

5. The method of claim 1, wherein the search waveform comprises an anodic phase preceding a leading cathodic phase, wherein the anodic phase has a lower amplitude absolute value than the leading cathodic phase.

6. The method of claim 1, wherein the therapy waveform comprises a multiphasic waveform comprising a leading anodic phase followed by a cathodic active charge recovery phase.

7. The method of claim 6, wherein an amplitude absolute value of the leading anodic phase is the same as an amplitude absolute value of the cathodic active charge recovery phase.

8. The method of claim 6, wherein an amplitude absolute value of the leading anodic phase is greater than an amplitude absolute value of the cathodic active charge recovery phase.

9. The method of claim 1, wherein the therapy waveform comprises a cathodic phase preceding a leading anodic phase, wherein the cathodic phase has a lower amplitude absolute value than the leading anodic phase.

10. The method of claim 1, wherein an amplitude absolute value of the leading phase of the therapy waveform is greater than an amplitude absolute value of the leading phase of the search waveform.

11. The method of claim 1, further comprising:
    determining a therapeutic window for stimulation using the first polarity,
    determining a therapeutic window for stimulation using the second polarity, and
    treating the patient with stimulation using whichever of the first polarity and the second polarity has the largest therapeutic window.

12. The method of claim 1, further comprising:
    determining an adverse effect threshold for stimulation using the first polarity,
    determining an adverse effect threshold for stimulation using the second polarity, and
    treating the patient with stimulation using whichever of the first polarity and the second polarity has the greatest adverse effect threshold.

13. The method of claim 1, further comprising:
    determining an indication of clinical effectiveness of stimulation using the first polarity,
    determining an indication of clinical effectiveness of stimulation using the second polarity, and
    treating the patient with stimulation using whichever of the first polarity and the second polarity has the greatest clinical effectiveness.

14. The method of claim 13, wherein the indications of clinical effectiveness comprise Unified Parkinson Disease Rating Scale (UPDRS) ratings.

15. The method of claim 1, further comprising:
    determining an indication of the patient's satisfaction with stimulation using the first polarity,
    determining an indication of the patient's satisfaction with stimulation using the second polarity, and
    treating the patient with stimulation using whichever of the first polarity and the second polarity has the greatest patient's satisfaction.

16. The method of claim 1, wherein the effective arrangement of electrodes comprises a single electrode at which the search waveform is applied.

17. The method of claim 1, wherein the effective arrangement of electrodes comprises a plurality of electrodes among which the search waveform is fractionated.

18. The method of claim 1, further comprising adjusting an amplitude value of the therapy waveform.

19. The method of claim 18, wherein the adjusting comprises lowering.

20. A non-transitory computer readable medium executable on an external controller configured to communicate with an implantable medical device (IMD) comprising an implantable pulse generator (IPG) and a leadwire implantable in a patient and comprising one or more electrodes, wherein the non-transitory computer readable medium comprises instructions, which when executed by the external controller, configure the external controller to:
- apply a search waveform at a plurality of arrangements of the one or more electrodes to determine an arrangement of electrodes and stimulation parameters that provides a therapeutic effect for the patient, and
- apply a therapy waveform based on the determined arrangement of electrodes and stimulation parameters, wherein
- the search waveform comprises a leading phase having a first polarity and an amplitude absolute value equal to or greater than an amplitude absolute value of any other phase of the search waveform, and wherein
- the therapy waveform comprises a leading phase having a second polarity opposite to the first polarity of the leading phase of the search waveform and having an amplitude absolute value equal to or greater than an amplitude absolute value of any other phase of the therapy waveform.

* * * * *